United States Patent [19]

Seitz et al.

[11] Patent Number: 5,371,250

[45] Date of Patent: Dec. 6, 1994

[54] PROCESS FOR THE PREPARATION OF PURE AQUEOUS BETAINE SOLUTIONS

[75] Inventors: Hubert Seitz; Reinhard Vybiral, both of Burgkirchen, Germany

[73] Assignee: Hoechst Aktiengesellschaft, Frankfurt, Germany

[21] Appl. No.: 120,281

[22] Filed: Sep. 13, 1993

[30] Foreign Application Priority Data

Sep. 25, 1992 [DE] Germany ............................ 4232157

[51] Int. Cl.$^5$ ........................................ C07C 231/100
[52] U.S. Cl. .......................................... 554/70; 554/52; 554/59; 554/41; 554/68; 554/69; 562/575
[58] Field of Search .................. 554/52, 69, 70, 41, 554/59, 68; 562/575

[56] References Cited

U.S. PATENT DOCUMENTS

| 3,819,539 | 6/1974 | Bloch et al. | 252/547 |
| 4,497,825 | 2/1985 | Bade | 514/556 |
| 5,075,498 | 12/1991 | Perine et al. | 562/575 |
| 5,239,095 | 8/1993 | Bade | 554/69 |

FOREIGN PATENT DOCUMENTS 259847 9/1988 German Dem. Rep. .

*Primary Examiner*—José G. Dees
*Assistant Examiner*—Deborah D. Carr
*Attorney, Agent, or Firm*—Connolly and Hutz

[57] ABSTRACT

The process described relates to the preparation of aqueous betaine solutions by reaction of a tertiary amine with an ω-monohalocarboxylic acid, preferably monochloroacetic acid, and an alkali metal hydroxide in the presence of water, which solutions are said to be highly pure particularly in respect of the tertiary starting amine and ω-monohalocarboxylic acid. This is achieved by first reacting the three reaction components in a certain molar ratio with the aim of obtaining a betaine solution which comprises only a tolerated amount of starting amine. This aqueous betaine solution is then treated with a sulfonating agent, preferably with an alkali metal sulfite, alkali metal pyrosulfite or alkali metal bisulfite, for conversion of the ω-monohalocarboxylic acid present into the corresponding sulfocarboxylic acid, which is not troublesome. The process described is simple to carry out and leads to the highly pure aqueous betaine solutions mentioned.

10 Claims, No Drawings

PROCESS FOR THE PREPARATION OF PURE AQUEOUS BETAINE SOLUTIONS

BACKGROUND OF THE INVENTION

1. Field of the Invention

The invention relates to a process for the preparation of pure aqueous solutions of betaines of the formula 1

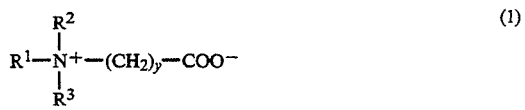

in which
- $R^1$ is an alkyl radical having 6 to 22 carbon atoms, preferably 8 to 18 carbon atoms, or a radical of the formula $R'CONH(CH_2)_z-$, in which $R'$ is an alkyl radical having 5 to 21 carbon atoms, preferably having 5 to 17 carbon atoms, and z is 2, 3 or 4,
- $R^2$ is an alkyl radical having 1 to 4 carbon atoms or a radical of the formula $-(CH_2)_m-OH$, in which m is 1, 2 or 3,
- $R^3$ is an alkyl radical having 1 to 4 carbon atoms or a radical of the formula $-(CH_2)_m-OH$ mentioned and
- y is 1, 2 or 3, by reaction of a tertiary amine of the formula 2

in which $R^1$, $R^2$ and $R^3$ have the meanings given, with an ω-halocarboxylic acid of the formula 3

in which X is a halogen, preferably Cl, and y has the meaning given, and with an alkali metal hydroxide in the aqueous phase.

DESCRIPTION OF THE PRIOR ART

The preparation of aqueous solutions of betaines by reaction (quaternization) of tertiary amines with an ω-halocarboxylic acid and an alkali metal hydroxide in the aqueous phase has already been known for a long time, for example from the two U.S. Pat. Nos. 3,819,539 and 4,497,825. It is based on the following overall equation (the reaction components are dimethyllaurylamine, monochloroacetic acid and sodium hydroxide):

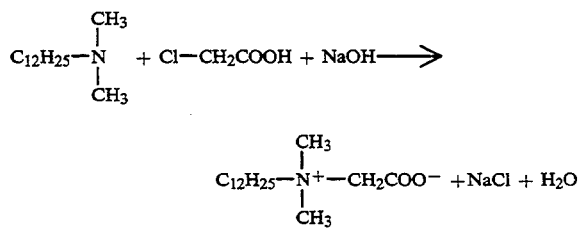

The resulting aqueous solutions essentially comprise the betaine required, the alkali metal halogen salt formed and the water employed and formed, and in general have an active compound content of 20 to 60% by weight, preferably 25 to 50% by weight. These aqueous betaine solutions are already valuable products as such (detergent bases), in particular in the field of body care. This is because, betaines have not only good cleansing properties but also a good skin tolerability.

In the preparation of the aqueous betaine solutions in question, it is a matter above all of obtaining the betaine in a high yield and high purity. In particular, the aqueous betaide solutions should be pure in respect of the starting amine and halocarboxylic acids (which is present as such and/or as the alkali metal salt), i.e. they should contain these compounds, if at all, only in a very small amount. Attempts have already often been made to achieve this aim by specific measures, thus, for example, by maintaining a particular pH during the quaternization, by bringing together the reaction components of tertiary amine, halocarboxylic acid and alkali metal hydroxide in a quite specific sequence, for example by initially introducing the tertiary amine and the halocarboxylic acid into the reaction vessel and slowly metering in the alkali metal hydroxide, or by initially introducing the halocarboxylic acid and the alkali metal hydroxide into the reaction vessel and metering in the tertiary amine, furthermore by using specific solvents and/or by maintaining a relatively low temperature during the reaction. All these attempts have not produced the desired success. The aqueous betaine solutions obtained by the known processes do not meet the purity requirements mentioned, which at the present time are becoming ever stricter.

SUMMARY OF THE INVENTION

The invention relates to a process for the preparation of pure aqueous solutions of betaines of the formula 1

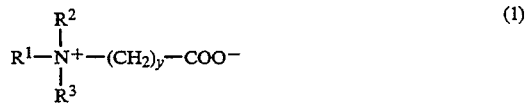

in which
- $R^1$ is an alkyl radical having 6 to 22 carbon atoms, preferably 8 to 18 carbon atoms, or a radical of the formula $R'CONH(CH_2)_z-$, in which $R'$ is an alkyl radical having 5 to 21 carbon atoms, preferably having 5 to 17 carbon atoms, and z is 2, 3 or 4,
- $R^2$ is an alkyl radical having 1 to 4 carbon atoms or a radical of the formula $-(CH_2)_m-OH$, in which m is 1, 2 or 3,
- $R^3$ is an alkyl radical having 1 to 4 carbon atoms or a radical of the formula $-(CH_2)_m-OH$ mentioned and
- y is 1, 2 or 3, by reaction of a tertiary amine of the formula 2

in which $R^1$, $R^2$ and $R^3$ have the meanings given, with an ω-halocarboxylic acid of the formula (3)

in which X is a halogen, preferably Cl, and y has the meaning given, and with an alkali metal hydroxide in the aqueous phase.

The object of the invention accordingly comprises providing a process for the preparation of the above-mentioned aqueous betaine solutions which produces the betaines in a high yield and high purity, i.e. aqueous betaine solutions comprising less than 1.5% by weight of tertiary amine, preferably less than 0.5% by weight, and comprising less than 50 ppm of ω-monohalocarboxylic acid, preferably less than 10 ppm.

DESCRIPTION OF THE PREFERRED EMBODIMENTS

The invention relates to a process for the preparation of pure aqueous solutions of betaines of the formula 1

$$R^1-\underset{\underset{R^3}{|}}{\overset{\overset{R^2}{|}}{N^+}}-(CH_2)_y-COO^- \tag{1}$$

in which
- $R^1$ is an alkyl radical having 6 to 22 carbon atoms, preferably 8 to 18 carbon atoms, or a radical of the formula $R'CONH(CH_2)_z-$, in which $R'$ is an alkyl radical having 5 to 21 carbon atoms, preferably having 5 to 17 carbon atoms, and z is 2, 3 or 4,
- $R^2$ is an alkyl radical having 1 to 4 carbon atoms or a radical of the formula $-(CH_2)_mOH$, in which m is 1, 2 or 3,
- $R^3$ is an alkyl radical having 1 to 4 carbon atoms or a radical of the formula $-(CH_2)_mOH$ mentioned and y is 1, 2 or 3, by reaction of a tertiary amine of the formula 2

$$R^1-NR^2R^3 \tag{2}$$

in which $R^1$, $R^2$ and $R^3$ have the meanings given, with an ω-halocarboxylic acid of the formula (3)

$$X-(CH_2)_y-COOH \tag{3}$$

in which X is a halogen, preferably Cl, and y has the meaning given, and with an alkali metal hydroxide in the aqueous phase.

The process according to the invention comprises first reacting the tertiary amines, the ω-monohalocarboxylic acid and the alkali metal hydroxide in a molar ration of 1:1 to 1.5:1 to 1.8, preferably 1:1.03 to 1.3:1 to 1.5, at a temperature of 60° to 98° C., preferably 70° to 95° C., and then treating the resulting aqueous betaine solution with a sulfonating agent at a pH of 7.5 to 13, preferably 8 to 10, and a temperature of 60° to 98° C., preferably 70° to 95° C., in order to convert the ω-monohalocarboxylic acid present in the aqueous betaine solution into the ω-sulfocarboxylic acid.

The process according to the invention is thus based on the combination of two specific process steps. In the first process step, the starting components of tertiary amine, ω-monohalocarboxylic acid and alkali metal hydroxide are employed in a selected molar ratio and the reaction is in general carried out until the low content of starting amine mentioned is obtained, i.e. until less than 1.5% by weight of tertiary amine, preferably less than 0.5% by weight of tertiary amine, based on the tertiary amine employed, is present in the resulting aqueous betaine solution. The use according to the invention of equimolar or excess halocarboxylic acid, based on the tertiary amine, thus gives rise to a reaction product which comprises only very little tertiary starting amine, if any. The aqueous betaine solution obtained in the first reaction step is therefore pure in respect of tertiary amine. However, it comprises halocarboxylic acid, which is present as such and, in particular, in the form of an alkali metal salt (for simplicity, acid is referred to below). In order to free the aqueous betaine solution also from the halocarboxylic acid, it is treated according to the invention with a sulfonating agent. The ω-monohalocarboxylic acid is thereby converted into the corresponding sulfocarboxylic acid. The following equation is intended to illustrate this, the halocarboxylic acid being monochloroacetic acid and the sulfonating agent being sodium hydrogen sulfite (it is understood that the acids mentioned are present as alkali metal salts):

$$Cl-CH_2COOH+NaHSO_3\rightarrow HSO_3-CH_2COOH+NaCl$$

In contrast to the ω-monohalocarboxylic acid (for example monochloroacetic acid), the sulfocarboxylic acid (sulfoacetic acid) is not a troublesome compound in the aqueous betaine solution, and in particular, in contrast to the ω-monohalocarboxylic acid, it is not toxic. After the sulfonation, an aqueous betaine solution is present which has the required purity both in respect of the tertiary amine and in respect of the halocarboxylic acid. It essentially comprises the betaine formed, the alkali metal halide and water and a greater or lesser amount of sulfocarboxylic acid in the form of an alkali metal salt, the betaine content (active compound content) being about 20 to 60% by weight, preferably about 25 to 50% by weight.

In the process according to the invention, the reaction between the tertiary amine and the ω-monohalocarboxylic acid in the presence of an alkali metal hydroxide and water is thus first carried out. The tertiary amine, the ω-monohalocarboxylic acid (which is in general employed in the form of a 60 to 80% strength by weight aqueous solution) and the alkali metal hydroxide (which is in general employed in the form of a 30 to 60% strength by weight aqueous solution, preferably 35 to 50% strength by weight aqueous solution) are employed in a molar ratio of 1:1.0 to 1.5:1.0 to 1.8, preferably in a molar ratio of 1:1.03 to 1.3:1.0 to 1.5. The amount of water (which is introduced as such and in the forte of the aqueous solutions of alkali metal hydroxide and halocarboxylic acid mentioned) is in general chosen such that the aqueous betaine solution obtained after the reaction has the abovementioned active compound content. The reaction temperature is 60° to 98° C., preferably 70° to 95° C. The reaction is in general maintained until no further tertiary starting amine is present in the aqueous betaine solution formed, or its content has fallen to the tolerated value. According to a preferred procedure, the tertiary amine and water in an amount such that a 15 to 55% strength by weight, preferably 20 to 45% strength by weight, aqueous solution of the tertiary amine in water is present are initially introduced into the reaction vessel. The mixture is heated to 60° to 98° C., preferably to 70° to 95° C. The ω-monohalocarboxylic acid and the alkali metal hydroxide are now added essentially simultaneously (continuously or in portions and separately from one another), in each case in the form of the aqueous solutions mentioned, while maintaining the temperature mentioned, after which the mixture is kept at this temperature for a further period until the required low amine content is reached. This reaction time is in general 5 to 30 hours. As regards the addition of halocarboxylic acid and alkali metal hydroxide, it has proved advantageous first to add the ω-halocarboxylic acid by itself and only to start addition of the alkali metal hydroxide when about 10 to 40 mol %, preferably about 15 to 30 mol %, of the ω-halocarboxylic acid has been added. Thus, after 10 to 40 mol %, preferably 15 to 30 mol %, of the total amount of ω-monohalocarboxylic acid to be employed has been introduced continuously or in portions into the amine/-water mixture, which is heated to 60° to 98° C., preferably 70° to 95° C., the alkali metal hydroxide and the remaining halocarboxylic acid are added essentially simultaneously (continuously or in portions and separately from one another) at the temperature mentioned. After addition of the alkali metal hydroxide and halocarboxylic acid, the mixture is kept at 60° to 98° C., preferably 70° to 95° C. for an after-reaction, in general until the low values mentioned for the tertiary starting amine are reached. The aqueous betaine solution thus obtained is still contaminated to a greater or lesser degree with ω-monohalocarboxylic acid.

The betaine solution still contaminated with ω-monohalocarboxylic acid is now treated with a sulfonating agent at a pH of 7.5 to 13, preferably 8 to 11, in order to convert the ω-monohalocarboxylic acid present (which is present in the form of an alkali metal salt) into the corresponding sulfocarboxylic acid (sulfocarboxylic acid alkali metal salt). The pH mentioned, if it is not in any case already present, is established by addition of alkali metal hydroxide or acid (for example hydrochloric acid). For the sulfonation, the mixture is brought to a temperature of 60° to 98° C., preferably to 70° to 95° C. This temperature as a rule already exists at the conclusion of the first reaction step (the quaternization). The customary sulfonating agents can be employed for the sulfonation. Suitable sulfonating agents are thus gaseous $SO_2$, $H_2SO_3$, alkali metal sulfite and alkali metal hydrogen sulfite, the alkali metal preferably being sodium or potassium. Of these sulfonating agents, the sulfites, pyrosulfites and bisulfites (hydrogen sulfites) are preferred and are in general employed in solid form or in the for of a 20 to 40% strength by weight aqueous solution. The amount of sulfonating agent, based on the amount of ω-monohalocarboxylic acid present, is as a rule 1 to 2.5 molar equivalents, preferably 1.3 to 2 molar equivalents. In detail, the sulfonation is preferably carried out such that the sulfonating agent is introduced all at once or continuously or in portions into the aqueous betaine solution, which is heated to 60° to 98° C., preferably 70° to 95° C., after which the solution is kept at the temperature mentioned until the desired low content of ω-monohalocarboxylic acid is reached. This reaction time is in general 1 to 4 hours. The product thus obtained is the aqueous betaine solution which is pure with respect to tertiary amine and monohalocarboxylic acid. If the sulfonating agent present as a result of an excess employed is undesirable, it can be oxidized, for example in the case of sulfite, with oxygen (air) or hydrogen peroxide to give the sulfate, and can thus be destroyed. After the oxidative treatment, an aqueous betaine solution which is also free from the sulfonating agent employed exists.

The following may also be noted in respect of the starting compounds of tertiary amine, ω-monohalocarboxylic acid and alkali metal hydroxide: the tertiary starting amines correspond to the abovementioned formula 2. The long alkyl radical $R^1$ can also contain double bonds, preferably 1 to 3. Preferred starting amines are those of the formula 2, if $R^1$ is an alkyl radical having 8 to 18 carbon atoms or a radical of the formula $R'CONH(CH_2)_z—$, in which $R'$ is an alkyl radical having 5 to 17 carbon atoms and z is 2, 3 or 4, and $R^2$ and $R^3$ are each methyl. Examples which may be mentioned are: dimethyloctylamine, dimethyllaurylaraine, dimethylstearylamine, dimethyl-coconut alkylamine, dimethyltallow alkylmine and the like, as well as lauroylaminopropyldimethylamine, stearoylaminopropyldimethylamine, coconut acylaminopropyldimethylamine and the like. The ω-halocarboxylic acid is preferably monochloroacetic acid. The alkali metal hydroxide is preferably sodium hydroxide or potassium hydroxide. The term "aqueous" betaine solution also comprises those solutions which also contain other solvents in addition to water, for example methanol, ethanol, propanol and/or isopropanol.

The process according to the invention has a number of advantages. It produces very pure aqueous betaine solutions. Betaine solutions which contain less than 0.5% by weight of tertiary amine (based on the amount of tertiary amine employed) and less than 50 ppm or even less than 10 ppm of ω-monohalocarboxylic acid can thus be obtained. The process according to the invention furthermore can also be carried out continuously, as well as discontinuously. The continuous procedure is preferably carried out in two to four stirred kettles arranged in cascade form.

The process according to the invention can thus be carried out discontinuously or continuously and produces betaine in a high yield and high purity.

The invention will now be illustrated in more detail by examples.

Example 1

188 g (0.587 mol) of coconut fatty acid amidopropyl-N,N-dimethylamine (based on hardened coconut fatty acid) and 345 g of water, i.e. 35% by weight of tertiary amine compound in water, are initially introduced into a 1 l glass flask fitted with a stirrer, thermometer, reflux condenser and dropping funnel. The mixture is heated to 82° C., while stirring. 72.8 g (0.616 mol) of an 80% strength by weight aqueous monochloroacetic acid (MCA) solution are slowly and continuously added dropwise to this suspension in the course of 5.5 hours. With a time delay of 30 minutes, after about 1/5 (20 mol %) of the total MCA solution has been added, 53.7 g (0.671 mol) of a 50% strength by weight aqueous NaOH solution are continuously added dropwise at the same time as the remaining MCA solution and separately therefrom (the molar ratio of tertiary amine compound, MCA and NaOH is 1:1.05:1.14). When the addition has ended, the mixture is allowed to after-react at 80° C. for 9 hours. The resulting 30% strength by weight aqueous betaine solution has a content of starting amidoamine of 0.14% by weight and of MCA of 0.13% by weight, i.e. 1300 ppm.

1.9 g (200 mol % or 2 molar equivalents, based on the residual MCA) of sodium bisulfite in the form of a 30% strength by weight aqueous solution are added to the resulting betaine solution, which has a pH of 10 to 11, at a temperature of 80° to 85° C., while stirring, after which the mixture is allowed to after-react at the temperature of 80° to 85° C. and at the pH of 10 to 11. After only 2 hours, an MCA content of less than only 5 ppm can be detected.

The aqueous betaine solution thus obtained, which is practically pure both in respect of starting amine and in respect of MCA, is brought to pH 5 with hydrochloric acid and stirred with 96 mol % of hydrogen peroxide (molar percentage based on the sodium bisulfite present) at 85° C. for 1 hour, in order to convert the excess sodium bisulfite into sodium sulfate. The desired pure aqueous 30% strength by weight betaine solution which is also free from sulfite is present.

Example 2

5.1 g (200 mol %, based on the MCA) of solid sodium sulfite (Na$_2$SO$_3$. 7H$_2$O) are added to 800 g of a 30% strength by weight coconut amidopropyl-N,N-dimethylcarboxymethylammonium-betaine solution prepared analogously to Example 1 and having a starting amidoamine content of only 0.15% by weight and an MCA content of 0.12% by weight or 1200 ppm and a pH of 10 to 11, and the mixture is stirred at 90° to 95° C. for 2 hours. An aqueous 30% strength by weight betaine solution containing sodium sulfite but less than 5 ppm of MCA and 0.15% by weight of starting amidoamine is present.

Example 3

150 g (0.664 mol) of lauryldimethylamine (70% by weight of C$_{12}$, 25% by weight of C$_{14}$ and 5% by weight of C$_{16}$) and 300 g of water, i.e. 33% by weight of tertiary amine compound in water, are initially introduced into a 1 l glass flask fitted with a stirrer, thermometer, reflux condenser and dropping funnel. The mixture is heated to 80° C., while stirring. 89.0 g (0.753 mol) of an 80% strength by weight aqueous monochloroacetic acid (MCA) solution are slowly and continuously added dropwise to this suspension in the course of 5.5 hours. With a time delay of 30 minutes, after about 1/5 (20 mol %) of the total MCA solution has been added, 66.0 g (0.825 mol) of a 50% strength by weight aqueous NaOH solution are continuously added dropwise at the same time as the remaining MCA solution and separately therefrom (the molar ratio of tertiary amine, MCA and NaOH is 1:1.13:1.24). When the addition has ended, the mixture is allowed to after-react at 80° C. for 10 hours. The resulting 30% strength by weight aqueous betaine solution has a content of starting amine (lauryldimethylamine) of 0.3% by weight, and of MCA of 0.2% by weight, i.e. 2000 ppm.

1.1 g (150 mol % or 1.5 molar equivalents, based on the residual MCA) of solid sodium pyrosulfite are added to the betaine solution obtained, which has a pH of 10 to 11, at a temperature of 80° to 85° C., while stirring, after which the mixture is allowed to after-react at the temperature of 80° to 85° C. and the pH of 10 to 11. After 4 hours, an MCA content of less than only 5 ppm is to be detected.

The aqueous betaine solution thus obtained, which is practically pure both in respect of the starting amine and in respect of MCA, is brought to pH 5 with hydrochloric acid and stirred with 96 mol % of hydrogen peroxide (molar percentages based on the sulfite present) for 1.5 hours at 85° C. in order to convert the excess sulfite into sulfate. The desired pure aqueous 30% strength by weight betaine solution which is also free from sulfite is present.

Examples 4 and 5

The corresponding betaine solutions are prepared analogously to Example 1 starting from octylamidopropyl-N,N-dimethylamine (Example 4) and laurylamidopropyl-N,N-dimethylamine (Example 5). The amount of residual MCA is brought to less than 5 ppm by reaction with sodium bisulfite as in Example 1.

Example 6

A 30% strength by weight betaine solution having a residual MCA content of 2000 ppm and a residual amine content of 0.3% by weight is prepared analogously to Example 3 starting from octyldimethylamine. A residual MCA content of less than 5 ppm is obtained by reaction with 2 molar equivalents of sodium sulfite, based on the residual MCA, as described in Example 3.

We claim:

1. A process for the preparation of a pure aqueous solution of a betaine of the formula 1

in which
R$^1$ is an alkyl radical having 6 to 22 carbon atoms, or a radical of the formula R'CONH(CH$_2$)$_z$—, in which R' is an alkyl radical having 5 to 21 carbon atoms, and z is 2, 3 or 4,
R$^2$ is an alkyl radical having 1 to 4 carbon atoms or a radical of the formula —(CH$_2$)$_m$—OH, in which m is 1, 2 or 3,
R$^3$ is an alkyl radical having 1 to 4 carbon atoms or a radical of the formula —(CH$_2$)$_m$—OH mentioned and
y is 1, 2 or 3, by reaction of a tertiary amine of the formula 2

in which R$^1$, R$^2$ and R$^3$ have the meanings given, with an ω-halocarboxylic acid of the formula 3

in which X is a halogen and y has the meaning given, and with an alkali metal hydroxide in the aqueous phase, which comprises first reacting the tertiary amine, the ω-monohalocarboxylic acid and the alkali metal hydroxide in a molar ratio of 1:1 to 1.5:1 to 1.8, at a temperature of 60° to 98° C. and then treating the resulting aqueous betaine solution with a sulfonating agent at a pH of 7.5 to 13 and a temperature of 60° to 98° C. in order to convert the ω-monohalocarboxylic acid present in the aqueous betaine solution into the ω-sulfocarboxylic acid.

2. The process as claimed in claim 1, wherein the tertiary amine, the ω-monohalocarboxylic acid and the alkali metal hydroxide are employed in a molar ratio of 1:1.03 to 1.3:1 to 1.5 and the reaction is carried out at a temperature of 70° to 95° C., and the aqueous betaine solution is then treated with a sulfonating agent at a pH of 8 to 11 and a temperature of 70° to 95° C.

3. The process as claimed in claim 1, wherein the reaction of tertiary amine, ω-monohalocarboxylic acid and the alkali metal hydroxide in the aqueous phase, wherein said aqueous phase contains water, is carried out in a manner in which the tertiary amine and the water in an amount such that a 15 to 55% strength by weight solution of tertiary amine in water is present are initially introduced into the reaction vessel, this mixture is heated to a temperature of 60° to 98° C. and first 10 to 40 mol % of the ω-monohalocarboxylic acid to be employed and then, essentially at the same time, the alkali metal hydroxide and remaining ω-monohalocarboxylic acid are introduced into the heated mixture, after which the mixture is kept a the temperature mentioned for after-reaction.

4. The process as claimed in claim 1, wherein the reaction of tertiary amine, ω-monohalocarboxylic acid and the alkali metal hydroxide in the aqueous phase, wherein said aqueous phase contains water, is carried out in a manner in which the tertiary amine and the water in an amount such that a 20 to 45 % strength by weight solution of the tertiary amine in water is present are initially introduced into the reaction vessel, this mixture is heated to a temperature of 70° to 95° C. and first 15 to 30 mol % of the ω-monohalocarboxylic acid to be employed and then, essentially at the same time, the alkali metal hydroxide and remaining ω-monohalocarboxylic acid are introduced into the heated mixture, after which the mixture is kept at a temperature mentioned for after-reaction.

5. The process as claimed in claim 1, wherein the sulfonating agent is employed in an amount of 1 to 2.5 molar equivalents, based on the ω-monohalocarboxylic acid present.

6. The process as claimed in claim 1, wherein the sulfonating agent is employed in amount of 1.3 to 2 molar equivalents, based on the ω-monohalocarboxylic acid present.

7. The process as claimed in claim 1, wherein an alkali metal sulfite, alkali metal pyrosulfite or alkali metal bisulfite is employed as the sulfonating agent.

8. The process as claimed in claim 1, wherein the aqueous betaine solution is treated with air or hydrogen peroxide after the sulfonation in order to destroy the residue of sulfonating agent present.

9. The process as claimed in claim 1, wherein the tertiary amine employed is one of the formula 2 where $R^1$ is an alkyl radical having 8 to 18 carbon atoms or a radical of the formula $R'CONH(CH_2)_z-$, in which $R'$ is an alkyl radical having 5 to 17 carbon atoms and z is 2, 3 or 4, and $R^2$ and $R^3$ are each methyl, the ω-monohalocarboxylic acid is monochloroacetic acid and the alkali metal hydroxide is sodium hydroxide or potassium hydroxide in the form of a 30 to 60% strength by weight aqueous solution.

10. The process as claimed in claim 1, wherein the aqueous phase contains water and the water is employed in a total amount such that the finished pure aqueous betaine solution contains 20 to 60% by weight of betaine, the percentages by weight being based on the aqueous betaine solution.

* * * * *